United States Patent [19]

Shearer et al.

[11] Patent Number: 5,437,677
[45] Date of Patent: Aug. 1, 1995

[54] GLENOID ALIGNMENT GUIDE

[75] Inventors: John R. Shearer, Hampshire; Philip Shelley, Sheffield, both of England

[73] Assignee: Minnesota Mining and Manufacturing Company, St. Paul, Minn.

[21] Appl. No.: 128,844

[22] Filed: Sep. 29, 1993

[30] Foreign Application Priority Data

Oct. 9, 1992 [GB] United Kingdom ............... 9221257

[51] Int. Cl.⁶ ............................................. A61B 17/56
[52] U.S. Cl. .................................. 606/96; 606/80; 606/86
[58] Field of Search .................. 606/96, 97, 98, 86, 606/80, 81, 90, 91, 99, 104, 105; 86; 623/16, 18, 19, 22, 23; 408/241 G, 241 S, 241 B, 238, 200, 202

[56] References Cited

U.S. PATENT DOCUMENTS

| | | |
|---|---|---|
| 4,230,117 | 10/1980 | Anichkov . |
| 4,421,112 | 12/1983 | Mains et al. . |
| 4,535,768 | 8/1985 | Hourahane et al. . |
| 4,632,111 | 12/1986 | Roche . |
| 4,672,957 | 6/1987 | Hourahane . |
| 4,708,139 | 11/1987 | Dunbar, IV ............... 606/96 |
| 4,722,330 | 2/1988 | Russell et al. . |
| 4,739,751 | 4/1988 | Sapega et al. ............. 606/96 |
| 4,759,350 | 7/1988 | Dunn et al. . |
| 4,787,377 | 11/1988 | Laboureau . |
| 4,883,048 | 11/1989 | Purnell et al. . |
| 4,920,958 | 5/1990 | Walt et al. . |
| 5,026,376 | 6/1991 | Greenberg ................. 606/96 |
| 5,030,219 | 7/1991 | Matsen, III et al. ....... 606/53 |
| 5,112,335 | 5/1992 | Laboureau et al. ....... 606/88 |
| 5,112,336 | 5/1992 | Krevolin et al. .......... 606/96 |
| 5,152,764 | 10/1992 | Goble ........................ 606/96 |
| 5,154,720 | 10/1992 | Trott et al. ................. 606/96 |
| 5,228,459 | 7/1993 | Caspari et al. ............. 128/898 |
| 5,312,412 | 5/1994 | Whipple .................... 606/96 |

FOREIGN PATENT DOCUMENTS

| | | |
|---|---|---|
| 350780 | 1/1990 | European Pat. Off. ............ 606/96 |
| 0380451 | 8/1990 | European Pat. Off. . |
| 0381893 | 8/1990 | European Pat. Off. . |
| 3339259 | 3/1985 | Germany . |
| 2147504 | 5/1985 | United Kingdom . |

OTHER PUBLICATIONS

Article entitled "Ring Retractor" by Fukuda et al.; The Journal of Bone and Joint Surgery, vol. 64-A, No. 2, Feb. 1982, p. 289.

Key, "Key Dual Bone Plate Outfit" Zimmer Fracture Appliance, Warsaw, Ind., Feb. 1, 1947.

*Primary Examiner*—Stephen C. Pellegrino
*Assistant Examiner*—Guy Tucker
*Attorney, Agent, or Firm*—Gary L. Griswold; Walter N. Kirn; Stephen W. Bauer

[57] ABSTRACT

A glenoid alignment guide for aligning a drill bit relative to the glenoid and the glenoid neck of a patient. The alignment guide comprises a retractor plate for displacing the posterior and superior aspect of the deltoid muscle, and a drill guide slidably movable along the retractor plate. The tip of a narrow, curved finger on the retractor plate is adapted to engage the bone of the glenoid neck to form a fulcrum for levering the muscle and other tissue clear of the glenoid. When the tip of the retractor plate engages the glenoid neck and the drill guide is advanced along the retractor plate against the glenoid face, the drill guide is adapted to guide a drill bit to make a hole from the glenoid face into the glenoid neck along the axis of the glenoid neck. This hole is then used to receive a fastener or locating peg of a glenoid component of a shoulder implant. The method of using the alignment guide is also disclosed.

18 Claims, 3 Drawing Sheets

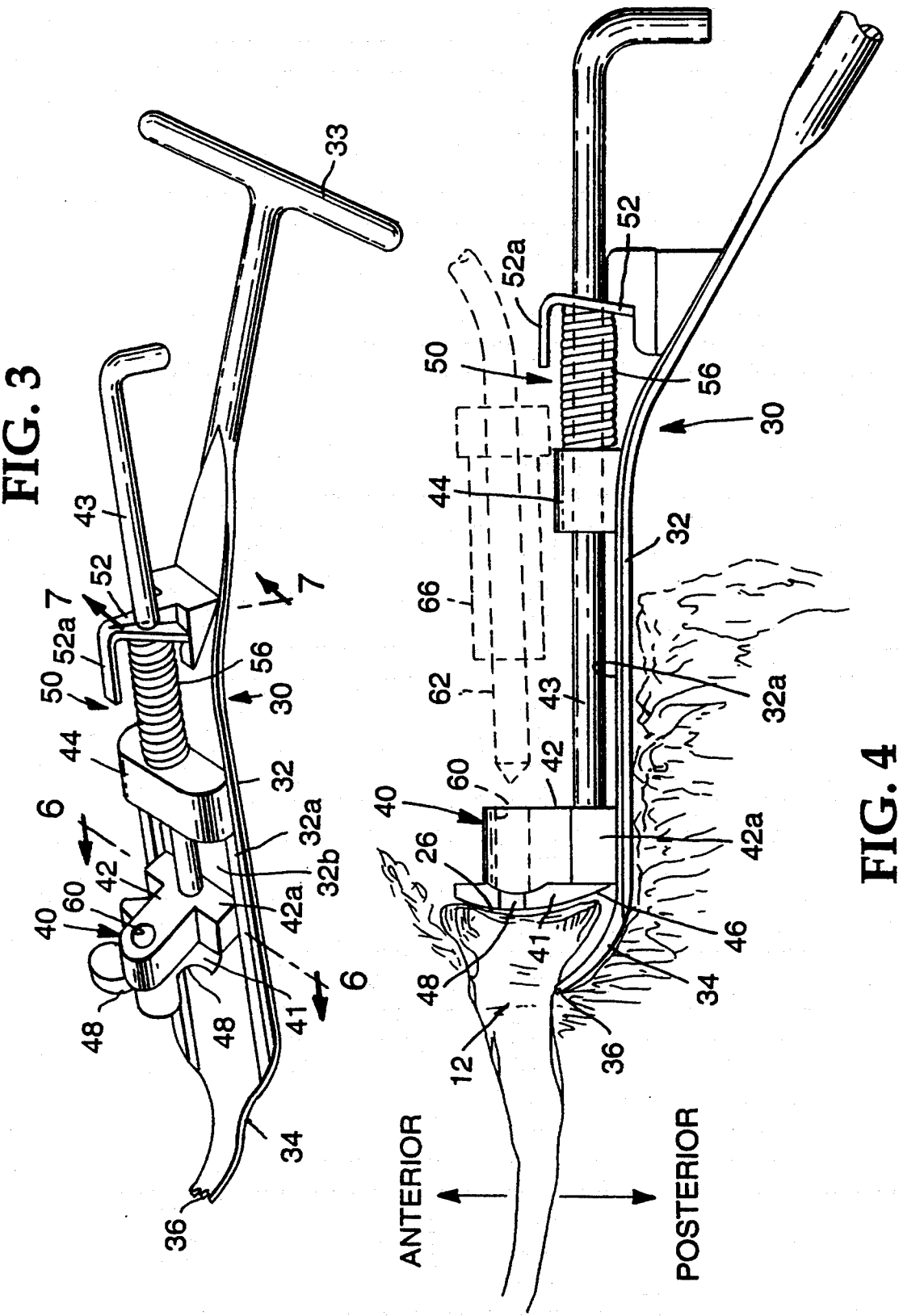

GLENOID ALIGNMENT GUIDE

This invention relates to a glenoid alignment guide to assist in the preparation of the glenoid during surgery to replace a shoulder joint with an implant.

BACKGROUND AND SUMMARY OF THE INVENTION

The preparation of the glenoid during shoulder surgery to receive a plastic or metal implant relies upon the surgeon being able to identify the axis of the bone and locate the implant within the maximum bone stock. Access to the glenoid is limited by the depth of the structure in the wound and the surrounding tissue as well as the surgical technique used.

The anatomy of the glenoid and scapula is such that there is very little bone into which an implant can be placed. The articulating surface of the joint consists of a shallow dished cartilaginous area bonded by soft tissue of the rotator cuff which stabilizes the humeral head against the glenoid.

The glenoid is roughly oval to pear-shaped and most replacement implants follow this contouring for optimal fit. Whilst the lateral aspect of the glenoid presents a broad surface for articulation, the margins taper rapidly medially to form a narrow neck of about 10 to 15 mm thickness from which emerge the coracoid (superiorly) and acromial (posteriorly) processes. The thinning of the glenoid progresses into the scapula bone where the thickness may be as little as 2 mm to 3 mm, although there is a broader spine running along the inferior margin of the scapula.

The axis of the visible face of the glenoid is easily identified, but does not correspond to the axis of the glenoid neck which is oriented posteriorly behind the glenoid face. The amount of bone in the neck in line with the axis of the visible glenoid is therefore greatly reduced and so it is along the actual axis of the glenoid neck that the anchoring means of the implant needs to be positioned. In addition, disease or degeneration can severely restrict the size of the glenoid, making implant placement more problematic. Further the scapula is a floating bone which is highly mobile, presenting little resistance to pressure, particularly under anaesthesia.

There are several problems for the accurate and satisfactory placement of an implant including:
1. access to the glenoid;
2. identification of the axis of the glenoid;
3. the alignment of the implant against the glenoid face,
4. the alignment of the anchoring means for the implant in the glenoid bone, and
5. the risk of glenoid neck fracture or exposure and penetration of the anchoring means through the wall of the bone.

To date the placement of an implant has depended upon the surgeon visually assessing the axis of the glenoid. He can gain access to and see the glenoid. However, the deltoid muscle, tendons and other tissue obscure the glenoid neck and it is undesirable to disturb this region unnecessarily. Therefore, the surgeon has had little or no actual knowledge of the anatomy behind the face of the glenoid, particularly the thickness and orientation of the neck which as noted above does not correspond with the axis of the glenoid. There is therefore always a risk that the anchoring device for the implant will either impinge on the sloping back wall of the neck which will lead to unsatisfactory placement of the implant against the glenoid face, or will penetrate the cortical bone which may result in bone fracture or interference with or damage to soft tissue.

The invention therefore has been made with these factors in mind. The invention provides a glenoid alignment guide adapted to retract soft tissue and muscle away for the glenoid, and guide a drill bit into the glenoid in proper alignment with the glenoid neck and glenoid face of a patient.

Generally, the glenoid alignment guide comprises a retractor plate for displacing the posterior and superior aspect of the deltoid muscle, and a drill guide slidably carried on the retractor plate. The retractor plate has a curved finger narrower than the plate defining the forward end of the retractor plate. The finger is adapted for insertion behind the glenoid. The tip of the finger is arranged to engage the bone of the glenoid neck to form a fulcrum for levering the muscle and other tissue clear of the glenoid. The drill guide defines an axial path along which a drill bit is guided. The drill guide is movable along the retractor plate to a forward position for engagement with the glenoid face. Guide means (e.g., a guide hole) is provided in the drill guide for guiding a drill bit along the axial path to make a hole from the glenoid face into the glenoid neck along the axis of the glenoid neck to receive fastening or locating means of a glenoid component of a shoulder implant. The tip of the retractor plate when engaged against the bone of the glenoid neck aligns the axial path defined by the drill guide relative to the glenoid neck.

Preferably, the tip of the finger has serrations adapted for non-slip engagement with the neck of the glenoid, and the tip of the finger is spaced radially from the center of the axial path defined by the guide means by 1.5 mm to 2.5 mm plus the radius of the drill bit to be guided by the guide means. Most preferably, the tip of the finger is spaced radially from the center of the axial path of the guide means by 2.0 mm to 2.5 mm plus the radius of the drill bit to be guided by the guide means.

Also, preferably, the glenoid alignment guide is adapted among other things for improved viewing of the glenoid face. For example, the drill guide may have a periphery and a plurality of cut away portions around the periphery to improve the view of the glenoid face as the drill guide is advanced. This allows the glenoid face to be viewed through the cut away portions of the drill guide to facilitate centering the drill guide relative to the glenoid face.

Most preferably, the drill guide has a generally convex-curved frontal surface adapted to correspond to the generally concave-curved surface of the glenoid face of the glenoid.

In one preferred aspect, locking means is provided for releasably locking the drill guide against the glenoid face of the glenoid. For example, the locking means may comprise a rod projecting rearwardly from the drill guide, a pivotable locking lever having a hole with an elongate cross section through which the rod passes, and resilient urging means for urging the locking lever such that the rod is gripped by the edges of the hole. The arrangement is such that retraction of the drill guide is resisted by the gripping of the rod by the locking lever but is possible if the locking lever is manually pivoted against the urging force of the resilient urging means to release the rod.

Most preferably, the retractor plate has a track mounting the drill guide on the retractor plate for sliding movement of the drill guide along the track in the axial direction. The track constrains the drill guide from rotation relative to the retractor plate, with the drill guide being mounted on the rod to move axially together with the rod to allow advancing the drill guide along the track of the retractor plate by manually moving the rod. For example, the retractor plate has a main body having opposite side edges, and ribs extending from the main body along the opposite side edges to define the track.

In yet another aspect, the drill guide has a rear surface, and a collar is fitted around the drill bit for engaging the rear surface of the drill guide to limit the penetration of the drill bit into the glenoid bone.

Such a guide can assist the surgeon in both obtaining good exposure of the glenoid and location for drilling a hole for fixing an implant. Thus the finger can be relatively narrow and so damage to nerves and blood vessels behind the glenoid can be kept to a minimum as it is inserted and its tip, when engaged with the bone, will identify the thinnest part of the glenoid neck so aligning the drill guide for optimum drilling. Thus the neck of the glenoid is of reasonably consistent width in all patients and once the tip of the finger engages it, one can be sure that the drill guide will be well positioned and ensure that, when the surgeon drills a hole, it will pass along the bone in the neck and not penetrate through the neck.

In a further aspect of the invention, referring to the method of using the glenoid alignment guide, the retractor plate is inserted between the patient's soft tissue and muscle and the glenoid, and the tip of the finger is placed against the glenoid neck. With the tip of the finger against the glenoid neck, the tissue and muscle is levered aside to expose the glenoid face, by means of the retractor plate. Then, with the tip of the finger remaining against the glenoid neck, the drill guide is advanced to a position where the drill guide abuts the glenoid face. With the tip of the finger remaining against the glenoid neck and the drill guide abutting the glenoid face, the drill guide is used to align a drill bit for drilling a hole along the axial center of the glenoid neck to receive fixing means of the implant.

BRIEF DESCRIPTION OF THE DRAWINGS

The invention will now be described, by way of example, with reference to the accompanying drawings, in which corresponding parts are indicated by corresponding reference characters, and in which:

FIG. 3 is a perspective view of a glenoid alignment guide according to the invention;

FIG. 4 is a side view of the glenoid alignment guide shown in position for aligning the drilling of a hole to receive an implant in the glenoid;

DETAILED DESCRIPTION OF A PREFERRED EMBODIMENT

Figure 1:
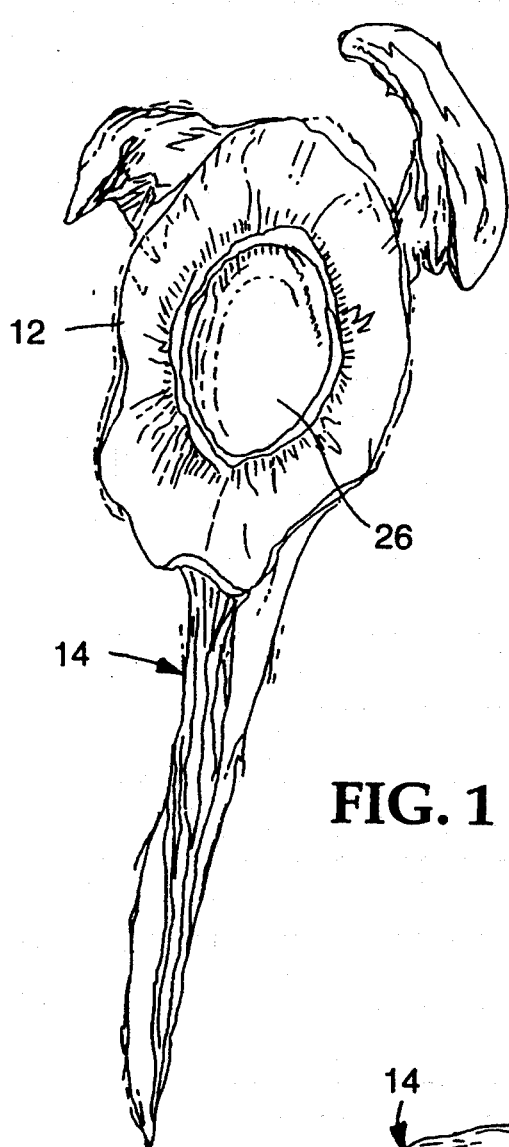
FIGS. 1 and 2 are views showing a human scapula.
Figure 2:
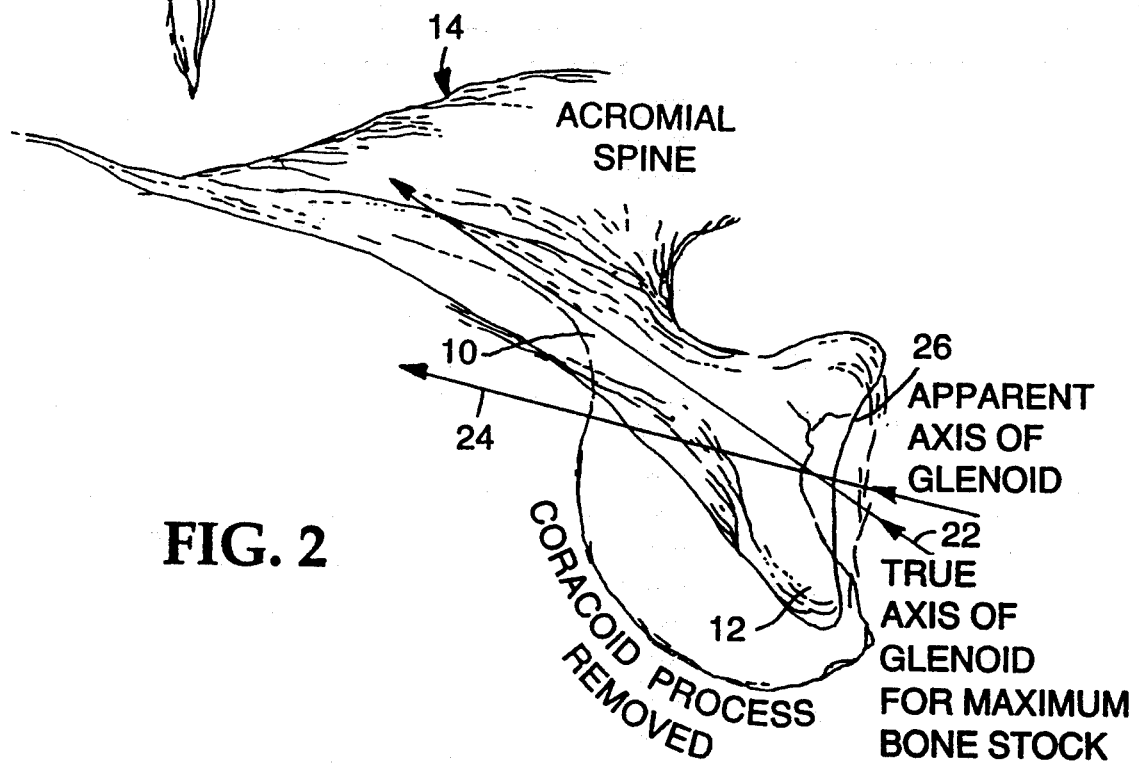

As can be seem from FIGS. 1 and 2, the neck 10 of the glenoid 12 of a human scapular 14 is very narrow, particularly as viewed in the superior orientation shown in FIG. 2. It is therefore important when making a drilled hole 63 into the glenoid 12 to receive the fixing screw of an implant, to ensure that the axis of the drilled hole 63 passes along the actual axis 22 of the glenoid 12, and not along the apparent axis 24 which is the one visible to a surgeon who can only see the articulating face 26 of the glenoid, the rest of the glenoid being covered by the deltoid muscle, tendons and other tissue, etc.

Figure 5:
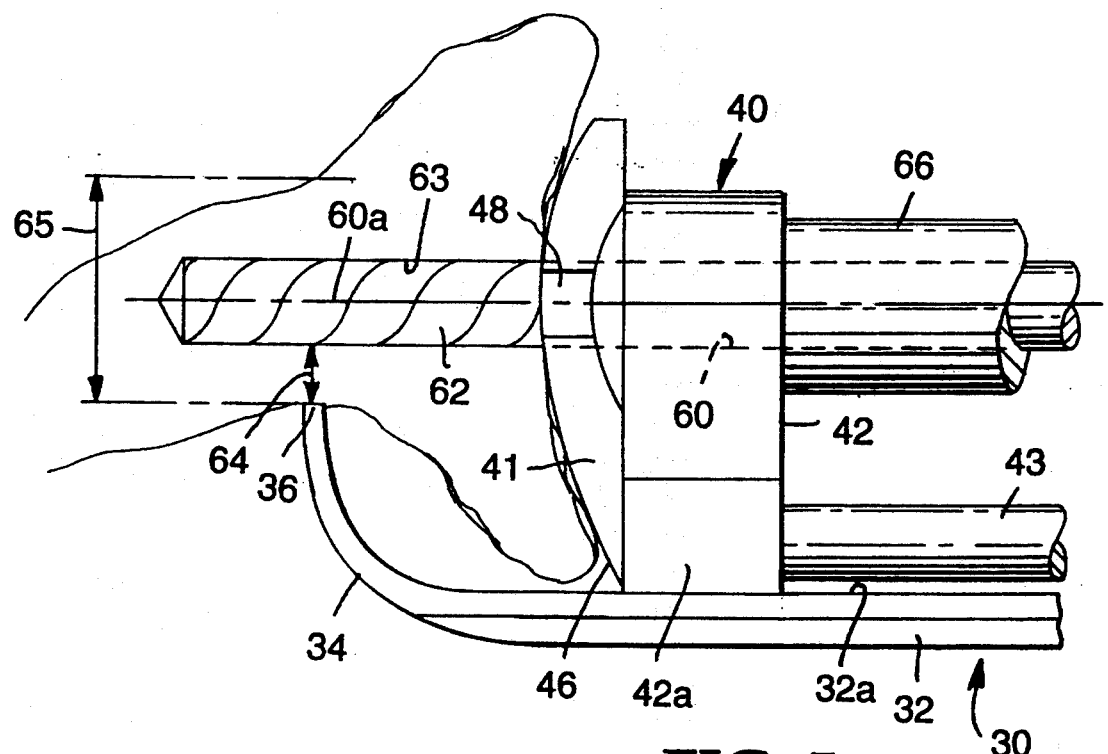
FIG. 5 is an enlarged detail of the glenoid alignment guide and glenoid shown in FIG. 4 and additionally showing the drilling of the hole.

In accordance with the invention a glenoid alignment guide 30 as shown in FIGS. 3 to 5 is used by a surgeon to assist in identifying this axis 22. This alignment guide 30 includes a retractor plate 32 which is used to displace the posterior and superior aspects of the deltoid muscle to assist in placing the glenoid alignment guide against the glenoid articulating face 26.

At its rear, the retractor plate 32 has a handle 33 to assist in manoeuvering the glenoid alignment guide 30, whilst at its front it has an integral curved finger 34 with a tip 36. This curved finger 34 acts as a fulcrum for the retractor plate 32 when the surgeon inserts the finger 34 behind the glenoid 12 and can then use the retractor plate 32 to lever muscle and the tissue clear of the glenoid face 26.

The finger 34 is narrower than the retractor plate 34 so as to reduce the damage to nerves and blood vessels which run behind the glenoid face 26. The tip 36 is not, however, pointed, or so narrow that it will penetrate into the bone as the powerful deltoid muscle is levered out of the way by the alignment guide 30. The tip 36 preferably has serrations as shown, or forked (not shown), to provide a secure non-slip engagement with the glenoid neck 10 so that the tip 36 does not slip as the muscle, etc. is being levered clear. The plate 32, therefore, assists the surgeons by ensuring that the glenoid 12 and particularly its face 26 are fully exposed.

The tip 36 of the finger 34 also serves as a guide. The surgeon locates the narrowest part of the glenoid neck with this finger 34. By ensuring that the tip 36 is kept in touch with this part of the bone, he can then ensure that the glenoid alignment guide 30 is located so that an eventual hole 63 drilled using the alignment guide 30, as will be described, will be along the axis 22 (FIG. 2), and so make best use of the available bone and will not break through the bone.

Figure 6:
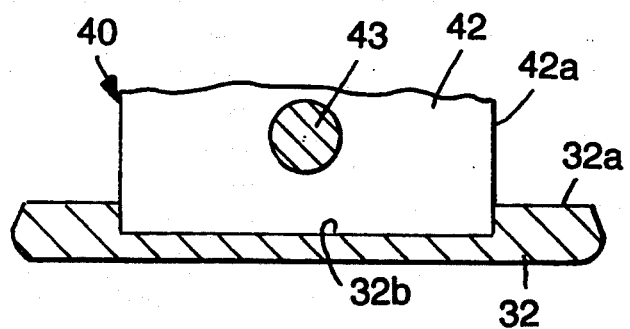
FIG. 6 is an enlarged cross-sectional detail taken along the line 6—6 of FIG. 3.

A drill guide 40 is slidably mounted on the retractor plate 32. The drill guide 40 includes a front portion 41 and an integral rear portion 42. The retractor plate 32 has upstanding ribs or edges 32a which, as best shown in FIG. 6, are slightly above the central surface 32b of the surface of the retractor plate 32 to define a track for slidably mounting the drill guide 40. These edges 32a engage side wing portions 42a extending from the rear portion 42 of the drill guide 40. Attached to and extending rearwardly from the rear portion 42 of the drill guide 40 is a rod or shaft 43 which is slidably mounted in a block 44 fixed to the retractor plate 32. The mounting of the shaft 43 and the engagement of the sides of the drill guide 40 with the edges 32a, ensures that the drill guide 40 is constrained to move axially along the retractor plate 32.

The front face 46 of the drill guide 40 is convex-curved and designed to engage and approximately match the generally concave-curved articulating face 26 of the glenoid. In addition three cut-outs 48 are provided to improve the surgeon's view of the face 26 when the drill guide 40 is brought to abut the face 26 as will be described. Thus, the cut outs 48 allow the surgeon to see the glenoid face and asses the correct size of implant to choose to be fitted. Further, the cut outs are positioned so as to coincide with the positioning of the small stabilizing screws which are used to prevent rotation of the fitted implant, and so facilitate the surgeon's assessment of whether one or more such screws can be satisfactorily positioned.

Figure 7:
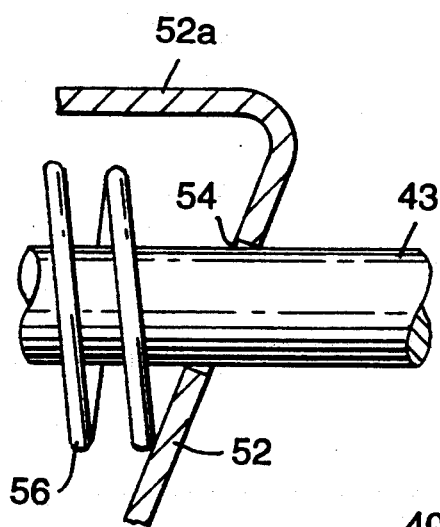
FIG. 7 is an enlarged cross-sectional detail taken along the line 7—7 of FIG. 3.

In order to lock the drill guide 40 in a selected position, a locking mechanism 50 is provided. This comprises a locking lever or clamp 52 pivotally mounted on the retractor plate 32, having a forwardly-bent portion 52a, and having a hole 54 having an elongate cross section (FIG. 7) through which the shaft 43 extends, and a coil spring 56 positioned around the shaft 43 between the block 44 and the clamp 52. The arrangement is such that the coil spring 56 normally pushes the locking clamp 52 in a rearward direction, the edges of the hole 54 clamping the shaft 43 and preventing its rearward movement. The drill guide 40 and shaft 43 can however be pushed forwardly since such movement will release the clamping action of the clamp 52 and temporarily overcome the spring force. In the event that the drill guide 40 is to be retracted, then one presses down on the forwardly-bent portion 52a which moves the locking clamp 52 forwardly against the action of the spring to release the shaft 43, so that the shaft and the drill guide 40 can be withdrawn.

Once the surgeon has positioned the tip behind the glenoid, then using the shaft 43, he pushes the drill guide 40 forwardly until its front face 46 contacts and presses firmly against the articulating face 26 of the glenoid 12, the cut outs 48 allowing the surgeon to see parts of the glenoid surface 26 to help ensure that tissue is not trapped between the face 46 and surface 26. This position is shown in FIGS. 4 and 5. The locking mechanism 52 then holds the drill guide 40 in that position.

As best shown in FIGS. 3 and 5, the drill guide 40 has a central through hole 60, and this is used to align a drill bit 62. The through hole 60 has a cross section sized to closely receive the drill bit 62 to provide adequate guidance of the drill bit 62. Therefore the surgeon can now drill a drilled hole 63 in the glenoid as shown in FIG. 5.

As can be seen from that figure, the axial path or axis 60a of the through hole 60 along which the drill bit 62 will be advanced is spaced approximately 2 mm to 2.5 mm plus the radius of the drill bit 62 from that tip 36 of the finger 34. In other words, the spacing 64 (FIG. 5) between path of the drill bit 62 and the tip 36 is preferably 2 mm to 2.5 mm. This ensures that hole 63 is made approximately in the center, in the sense viewed in FIG. 5, of the glenoid neck 10.

Since the through hole 60 is sized to closely receive the drill bit 62, one alternative way of expressing this is that the tip 36 of the finger 34 is spaced from the extended central axis 60a of the through hole 60 by a distance approximately equal to the radius of the through hole 60 plus 2 mm to 2.5 mm.

More specifically, the glenoid neck 10 has a dimension, in the direction of the arrow 65 (FIG. 5), which is typically 10 mm and almost never more than 12 mm. Assuming therefore that the drill bit 62 has a diameter of 5 mm, this leaves a thickness of 5 mm, or exceptionally, 7 mm of bone, and so 2.5 mm, i.e., half the typical 5 mm of available bone, is the preferred maximum spacing of the tip 36 of the finger 34 from what will be the hole 63 which is drilled. In case the dimension of the glenoid neck 10 may be slightly less than 10 mm, however, this spacing 64 should be less than that maximum, e.g., 2 mm, and desirably no less than 1.5 mm. By choosing the spacing 64, to be 1.5 mm to 2.5 mm and most preferably approximately 2 mm, one can therefore ensure that the drilled hole 63 is approximately centered in the glenoid neck 10 in the sense of the arrow 65.

The alignment of the drilled hole 63 in the sense transverse to the direction of the arrow 64, is not as critical and so small variations of the alignment of the drilled hole 63 in the sense transverse to the plane of the FIG. 5, is not usually too critical.

A cylindrical sheath or collar 66 is fitted over the drill bit 12 before it is inserted through the through hole 60 of the drill guide 40. This collar 66 prevents excessive drilling of the glenoid 12 since it will engage the rear face of the drill guide 40 when the depth of the drilled hole 63 is sufficient, normally 20 to 25 mm. Thus the drill bit 12 should not be allowed to penetrate through the back of the scapular.

Therefore the through hole 60 of the drill guide 40 guides and aligns the axis of the drilled hole 63 which is drilled and the sheath 66 abuts the rear face of the rear portion of the drill guide 40 when the hole 63 has been drilled to sufficient depth, so limiting the depth of the drilled hole 63. Both arrangements therefore prevent the drill bit 12 and drilled hole 63 from breaking through the neck 10.

The drill guide 40 can thereafter be retracted and the alignment guide 30 removed to allow subsequent steps in the fitting of the implant which may include preparation of the glenoid articulating surface, tapping of the hole 63, and securing of the implant by screwing into the tapped hole 63. These steps form no part of the present invention and so need no further explanation. They are, however, steps which are known and understood by the surgeon.

Co-assigned British Patent Application No. 2 251 795 discloses a preferred shoulder implant, and is hereby incorporated by reference. See, also, the U.S. counterpart to that application, Ser. No. 08/035,906, filed Mar. 23, 1993, by John R. Shearer and Philip Shelley, on "Orthopedic Implant" which is a continuation of Ser. No. 07/822,619, filed Jan. 17, 1992, which is also hereby incorporated by reference.

As various changes could be made in the above constructions and methods without departing from the scope of the invention, it is intended that all matter contained in the above description or shown in the accompanying drawings be interpreted as illustrative and not in a limiting sense.

We claim:
1. A glenoid alignment guide for aligning a drill bit relative to the glenoid and the glenoid neck of a patient, the glenoid alignment guide comprising:
a retractor plate for displacing the posterior and superior aspect of the deltoid muscle, the retractor plate having a handle, a main body and a curved finger narrower than the main body of the retractor plate defining the forward end of the retractor plate, the finger being adapted for insertion behind the glenoid, the finger having a tip arranged to engage the bone of the glenoid neck to form a fulcrum for levering the muscle and other tissue clear of the glenoid, the main body of the retractor plate having opposite sides including a first side for engagement with the deltoid muscle, and a second side opposite the first side; and
a drill guide slidably carried on the retractor plate only along the second side of the main body of the retractor plate and defining an axial path along which a drill bit is guided, the drill guide being movable along the second side of the main body of retractor plate to a forward position for engagement with the glenoid face, the arrangement being such that the drill guide can be advanced along the second side of the main body while the first side of the main body is engaging the deltoid muscle, and having guide means for guiding a drill bit along the axial path to make a hole from the glenoid face into the glenoid neck along the axis of the glenoid neck to receive fastening or locating means of a glenoid component of a shoulder implant, the tip of the finger of the retractor plate when engaged against the bone of the glenoid neck aligning the axial path defined by the drill guide relative to the glenoid neck.

2. A glenoid alignment guide according to claim 1 in which the tip of the finger has serrations adapted for non-slip engagement with the neck of the glenoid.

3. A glenoid alignment guide according to claim 2 in which the tip of the finger points in a direction that is generally perpendicular to the second side of the main body.

4. A glenoid alignment guide according to claim 2 in which the tip of the finger points in a direction that is generally perpendicular to the axial path defined by the drill guide.

5. A glenoid alignment guide according to claim 1 in which the axial path defined by the drill guide has a center, the guide means comprising a through hole in the drill guide having a radius adapted to closely receive and guide a drill bit, the tip of the finger being spaced radially from the center of the axial path defined by the drill guide by 1.5 mm to 2.5 mm plus the radius of the through hole in the drill guide.

6. A glenoid alignment guide according to claim 5 in which the tip of the finger is spaced radially from the center of the axial path defined by the drill guide by 2.0 mm to 2.5 mm plus the radius of the through hole in the drill guide.

7. A glenoid alignment guide according to claim 1 adapted among other things for improved viewing of the glenoid face, the drill guide having a periphery and a plurality of cut away portions around the periphery extending laterally inwardly relative to the axial path defined by the drill guide to improve the view of the glenoid face as the drill guide is advanced.

8. A glenoid alignment guide according to claim 7 in which the drill guide has a generally convex-curved frontal surface having a curvature substantially corresponding to the generally concave-curved surface of the glenoid face of the glenoid.

9. A glenoid alignment guide according to claim 1 further comprising locking means for releasably locking the drill guide against the glenoid face of the glenoid.

10. A glenoid alignment guide according to claim 9 in which the tip of the finger and the guide means define forward and rearward directions, respectively, along the alignment guide; the locking means comprising:
a rod projecting rearwardly from the drill guide;
a pivotable locking lever having a hole with an elongate cross section through which the rod passes; and
resilient urging means for urging the locking lever such that the rod is gripped by the edges of the hole, so that retraction of the drill guide is resisted by the gripping of the rod by the locking lever but is possible if the locking lever is manually pivoted against the urging force of the resilient urging means to release the rod.

11. A glenoid alignment guide according to claim 10 in which the retractor plate has a track on the second side of the main body mounting the drill guide on the retractor plate for sliding movement of the drill guide along the track in the axial direction, the track constraining the drill guide form rotation relative to the retractor plate, the drill guide being mounted on the rod to move axially together with the rod to allow advancing the drill guide along the track of the retractor plate by manually moving the rod.

12. A glenoid alignment guide according to claim 11 in which the main body of the retractor plate has opposite side edges, and ribs extending from the main body along the opposite side edges to define the track.

13. A glenoid alignment guide according to claim 1 in which the drill guide has a rear surface, the glenoid alignment guide further comprising a drill bit received and guided by the drill guide, and a collar fitted around the drill bit for engaging the rear surface of the drill guide to limit the penetration of the drill bit into the glenoid bone.

14. A glenoid alignment guide according to claim 1 in which the drill guide has a generally convex-curved frontal surface having a curvature substantially corresponding to the generally concave-curved surface of the glenoid face of the glenoid.

15. A glenoid alignment guide according to claim 1 in which the finger curves toward a direction that is generally perpendicular to the second side of the main body.

16. A glenoid alignment guide according to claim 15 in which the tip of the finger points in a direction that is generally perpendicular to the second side of the main body.

17. A glenoid alignment guide according to claim 15 in which the tip of the finger points in a direction that is generally perpendicular to the axial path defined by the drill guide.

18. A glenoid alignment guide according to claim 15 in which the finger is substantially narrower than the main body.

* * * * *

UNITED STATES PATENT AND TRADEMARK OFFICE
CERTIFICATE OF CORRECTION

PATENT NO. : 5,437,677

DATED : August 1, 1995

INVENTOR(S) : John R. Shearer and Phillip Shelley

It is certified that error appears in the above-indentified patent and that said Letters Patent is hereby corrected as shown below:

On the title page:

Under section [56] "References Cited - U.S. Patent Documents"
add the following:

```
1,985,108  12/1934  Rush
2,181,746  11/1939  Siebrandt
2,291,413   7/1942  Siebrandt
2,362,957  11/1944  Hackett
3,835,849   9/1974  McGuire
4,444,180   4/1984  Schneider et al.
4,633,862   1/1987  Petersen
4,706,660  11/1987  Petersen
5,002,547   3/1991  Poggie et al...............606/88
5,021,055   6/1991  Burkinshaw et al..........606/82
5,108,401   4/1992  Insall et al..............606/79
```

UNITED STATES PATENT AND TRADEMARK OFFICE
CERTIFICATE OF CORRECTION

PATENT NO.   : 5,437,677
DATED        : August 1, 1995
INVENTOR(S)  : John R. Shearer and Phillip Shelley It is certified that error appears in the above-indentified patent and that said Letters Patent is hereby corrected as shown below:

On the title page:

Under section [56] "References Cited - U.S. Patent Documents"
    add the following:
    5,129,908   7/1992  Petersen..................606/88
    5,147,365   9/1992  Whitlock et al............606/88
    5,250,050  10/1993  Poggie et al..............606/79

Signed and Sealed this

Fourth Day of June, 1996

Attest:

BRUCE LEHMAN

*Attesting Officer*  *Commissioner of Patents and Trademarks*